United States Patent [19]
>
> Capo-Gual et al.

[11] Patent Number: 4,597,651

[45] Date of Patent: Jul. 1, 1986

[54] APPARATUS FOR THE DETECTION OF EYE SIGHT DEFECTS AND CASSETTE FOR THE OPERATION OF SUCH AN APPARATUS

[75] Inventors: Christine Capo-Gual, Sevran; Luc Delattre, Pont Sainte Maxence; Jean-Claude Hennequin, Lizy sur Ourcq, all of France

[73] Assignee: Essilor International (Compagnie Generale d'Optique), Creteil, France

[21] Appl. No.: 522,230

[22] Filed: Aug. 11, 1983

[30] Foreign Application Priority Data

Aug. 27, 1982 [FR] France .................................. 82 14745

[51] Int. Cl.$^4$ ................................................. A61B 3/02
[52] U.S. Cl. .................................... 351/243; 351/239; 351/244
[58] Field of Search ............... 251/239, 240, 243, 237, 251/244; 351/200

[56] References Cited

U.S. PATENT DOCUMENTS 2,798,408 7/1957 Ellis et al. .
3,684,355 8/1972 Molner ................................. 351/243
3,861,790 1/1975 Tamura .
3,891,311 6/1975 Fletcher et al. .
3,905,688 9/1975 Decker et al. ....................... 351/243

FOREIGN PATENT DOCUMENTS 2301215 1/1976 France .
2437818 10/1978 France .
1385675 2/1975 United Kingdom .

*Primary Examiner*—Rodney B. Bovernick
*Assistant Examiner*—D. M. Dzierzynski
*Attorney, Agent, or Firm*—Burgess, Ryan & Wanye

[57] ABSTRACT

The present invention relates to an apparatus for eye sight examination, allowing to test both of the patient's eyes, especially to detect his common failures and vision defects, for far and close vision, and eventually intermediary distance vision.

The test-image are borne by at least one ribbon or band mounted in a block of two winding spools, housed in a body forming an easily removable tape box of an adequate support of body of the apparatus.

The invention applies to the automatic or semi-automatic detection of visual defects of a patient.

10 Claims, 6 Drawing Figures

APPARATUS FOR THE DETECTION OF EYE SIGHT DEFECTS AND CASSETTE FOR THE OPERATION OF SUCH AN APPARATUS

BACKGROUND OF THE INVENTION

The present invention relates to an apparatus for testing the sight of a patient in order to detect the visual defects and faults of vision of each of the eyes of this patient, by viewing successive test images presented for close sight, far sight and intermediary sight with the use of a system of mirrors and/or lenses.

DESCRIPTION OF THE PRIOR ART

It is known to use devices for detecting vision defects at far sight and at close sight by examining the test-images located within the housing of the apparatus, via an optical circuit comprising lenses or, preferably, one or several mirrors and inclined semi-reflecting blades or prisms. The test-images used can be supported by drums or rotary plates and a system of screens or blinds can uncover the optical circuit or the images that it is desired to use for the examination of the patient's sight.

These detection apparatus that allow a thorough examination of the sight, even in stereoscopic vision, nevertheless present various shortcomings with respect to modern conditions for sight examination.

Indeed, depending on the age of the patients and the types of vision defects to be detected, it is sometimes necessary to have available a large number of test-images that cannot all be set out on the rotary drums or discs. For the examination of a patient's sight, it is furthermore indispensible with known apparatus to have this patient followed by an operator during the test, which thus considerably increases the cost of a complete test and discourages numerous patients from undergoing or renewing a vision test due to the financial or physical restrictions of this examination.

One of the aims of the present invention is precisely to allow to reduce the cost of a thorough sight examination and to allow to realize it in the best conditions of comfort for the patient, the presentation of the tests being programmed in advance as a function of the data of the patient whose view is to be checked.

SUMMARY OF THE INVENTION

With this aim, the apparatus for the examination of the view allows to test the two eyes of the patient, especially to detect his visual deficiencies with the use of a system of mirrors and/or lenses interposed on the test or target image vision circuit (texts or designs), and comprising two different vision paths for examining close sight and far sight, is characterized in that it possibly comprises, according to the invention, a third path for examining sight at intermediary distance, and in that the test or target images are carried by at least one ribbon or film mounted in a block of two winding spools housed in a body forming a tape box or cassette easily removable from an adequate support of the body of the apparatus, one at least of said spools being adapted to be driven in rotation in order to successively passing a series of test or target images on a part of the ribbon or film that is stretched between the two spools and which is displaced so as to be placed in front of the test-image input openings on the circuit or the vision path and which are provided on the body of the tape box and, in a coincident manner, on the body of the apparatus.

When the apparatus comprises at least one path for far vision and at least one other path for intermediary distance vision, these paths are equipped with concave spherical mirrors adapted to allow the vision of a single test-image indifferently on each of the two paths and thus allow to use on the film or the ribbon only a single test-image for far vision and intermediary vision.

Each of the vision paths comprises, on the side of the patient, two openings, each opening able to be occulted individually or in combination with other openings by any adequate means such as a mobile screen.

Preferably, the body of the removable tape box contains means for lighting the test-image ribbon or film by the rear according to the vision of the patient, and means for manually or automatically connecting a feed source, such as an electric network, to these lighting means and to driving means for rotating the spool of the box.

According to another embodiment of the invention, the said apparatus comprises a loud-speaker circuit associated to the rotation of the spools of the tape box in order to give instructions and/or ask questions to the patient during the move of the test-image bank.

In order to allow the patient to achieve himself the bank of vision tests, the apparatus according to the invention may comprise a recording circuit of the patient's responses to the questions of the loudspeaker circuit which is associated and/or synchronized to the rotation of the spools of the tape boxes.

The processing of the patient's responses can be carried out in an easier manner when the recording circuit of the patient's responses to the questions of the loudspeaker circuit comprises a recording band that reels off in synchronization with the test-images film or ribbon.

The reeling off speed of the tests is directly linked to the rythm followed by the patient. A given test only appears once the patient has replied to the presentation of the preceding test.

It is also possible to provide for rewinding the test band when the patient has not understood the question.

Occultation means of the openings of each path are directly linked to the test presented and are thus programmed in function of this test.

According to another embodiment of the apparatus according to the invention, it comprises punctual or semi-punctual light sources, such as LED diodes, allowing to detect the defects in the visual field of the patient and the possible punctual defects of his retina.

According to another embodiment, the apparatus comprises a vision chamber receiving the head of the patient and equipped with an adjustable rest for the patient's forehead allowing him to maintain, during the course of examination, the centre of rotation of each of his eyes, substantially coinciding with the point of convergence of the paths of vision corresponding to each eye.

The vision chamber receiving the patient's head is preferably equipped with lighting and/or reflection means able to produce a luminous environment allowing to adapt the eyes of the patient to given lighting conditions by simulating a variable lighting zone surrounding the test. It is thus possible artificially to create conditions of luminous surroundings of the working position of an individual and to detect its influence on his vision.

When sufficient lighting levels are available, it is also possible to use the surroundings for glare sensitivity tests.

According to one more elaborate embodiment of the device, the spool or the film of the tape box or cassette is adapted to be driven for reeling off at an easily adjustable speed in order to allow to test the aptitude of the patient for visioning passing images.

The removable tape box or cassette comprising the ribbon or the film can be fixed on the body of the apparatus in a position causing this ribbon or film to pass in a substantially vertical or horizontal direction with respect to the patient's eyes, or may be adapted to be fixed on the body of the apparatus selectively in any one of these two perpendicular positions.

According to another more elaborate embodiment, the removable tape box or cassette comprising the ribbon or the film and fixed on the body of the apparatus is adapted to be easily oriented in a plurality of positions in a displacement plane of the ribbon or the film so as to allow the ribbon or the film to pass according to a plurality of corresponding directions comprising vertical and horizontal directions with respect to the patient's eyes as well as a plurality of intermediary directions, and in order to allow the ribbon or the film to pass in all directions, the tape box bears its own driving motor of the ribbon or the film connected to adequate adjustable remote control means such as a flexible or sliding electrical connection.

According to various embodiments of the tape boxes used on the apparatus according to the invention for detecting sight defects, the tape box comprises between its spools at least one stretcher roll applied on the part of the ribbon or the film stretched between the two spools, and the body of the tape box has, for each image-test, an opening having suitable dimensions.

The apparatus may comprise a cell for detecting the position of the ribbon.

According to another particularly practical embodiment of tape boxes for the apparatus according to the invention, one of the spools of the tape box is constantly urged back to the wound position by a spring, such as a torsion spiral spring, whereas another spool is connected, at least in service position on the apparatus, to an unreeling motor such as an electric motor, via an irreversible transmission, in such a manner that in service position on the device, the band or the film of the tape box is constantly taut and can nevertheless be displaced and stopped at a given point of the test-images bank.

BRIEF DESCRIPTION OF THE DRAWINGS

Other aims, advantages and features of the device for detecting sight defects according to the invention will appear from the following description, given by way of non-limitative example, of a preferred embodiment of the device and its tape box-type bearing a bank of tests, reference being made to the appended drawings in which.

DESCRIPTION OF THE PREFERRED EMBODIMENT

Figure 1:
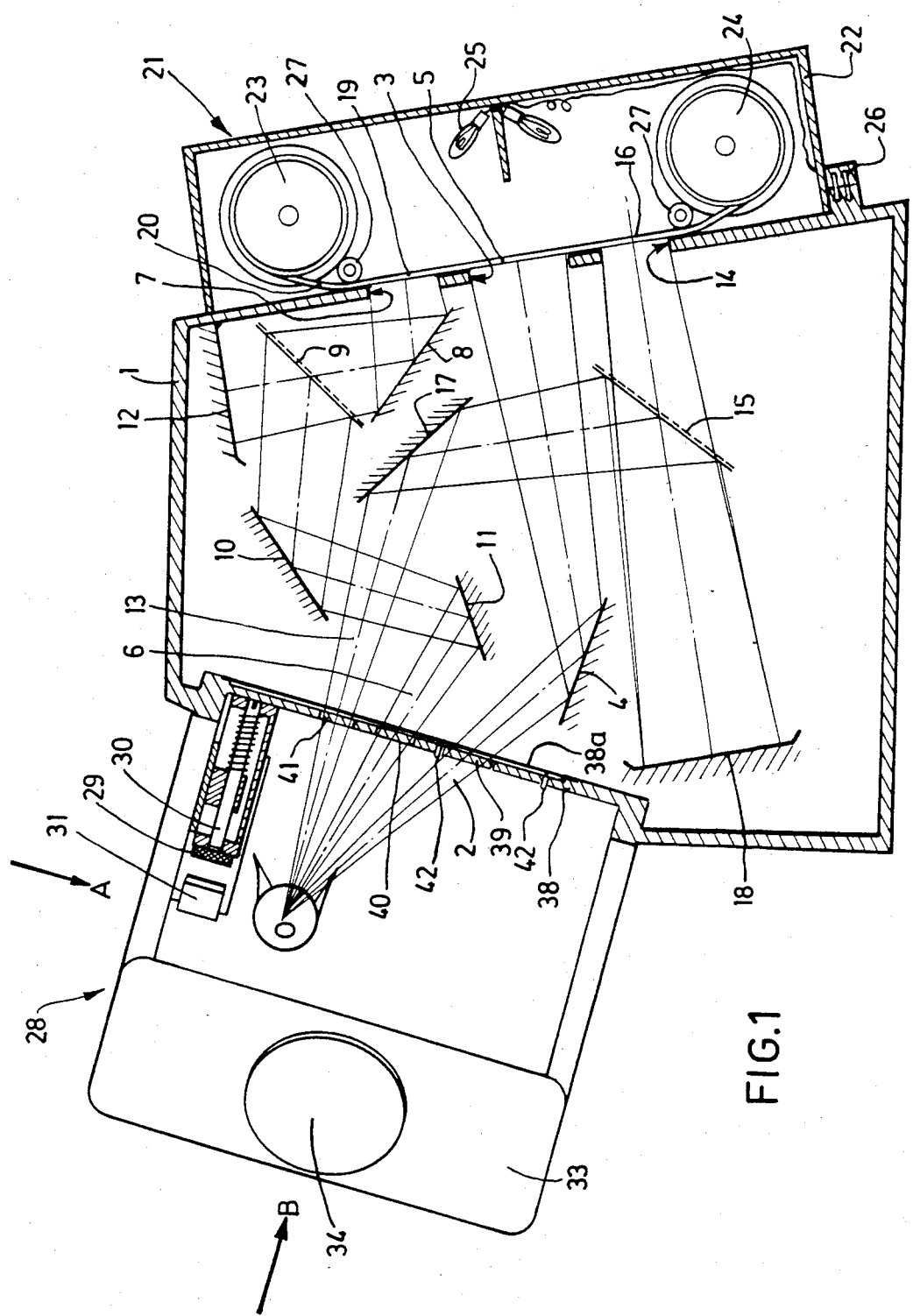
FIG. 1 shows a schematic cross-section of the apparatus according to the invention equipped with its utilisation tape box.

FIG. 1 shows the apparatus according to the present invention mounted in a body 1 made of a convenient materiel such as plastic material, and which comprises on internal supports various vision circuits or paths that all reach the centres 0 of each of the patient's eyes to be examined. Close vision path 2 issues from an opening 3 provided in the body of the apparatus and it is sent back onto a plane mirror 4 in order to define a travel-distance of about 30 to 40 centimeters for light rays issuing from an image 5 at close vision. Intermediary distance vision path to comprises, from an opening 7 in body 1, a series of plane mirrors 8, 10, 11 on the luminous travel-distance of which is interposed a semi-reflecting mirror 9 that allows to pass luminous rays towards a concave spherical mirror 12 allowing to place the image at a distance. The far vision path 13 comprises, from an opening 14 in body 1, a semi-reflecting mirror 15 that sends back the luminous beam issued from the image in far vision 16 on a plane mirror 17, after reflection on a concave mirror 18.

According to the invention, the test or target images 5 for close vision, 19 for intermediary distance vision (of about 0.7 meter) and 16 for far vision, are carried by the film or ribbon 20 of a tape box or cassette 21 in the body 22 of which are mounted two winding spools 23 and 24 bearing film 20 and lighting means of this film 20 such as lamps 25 fed by electric current by run-through plugs or terminals 26 that cooperate with the corresponding terminals and/or plugs of body 1 of the apparatus.

Figure 5:
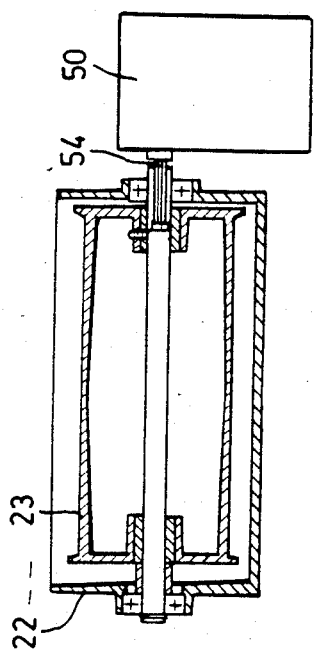
FIG. 5 is a partial cross-section of one of the spolls of the tape box according to FIG. 4; and, FIG. 6 is a cross-section of the other spool of the tape box.
Figure 6:
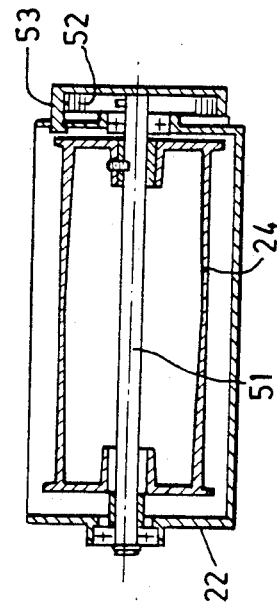
Figure 4:
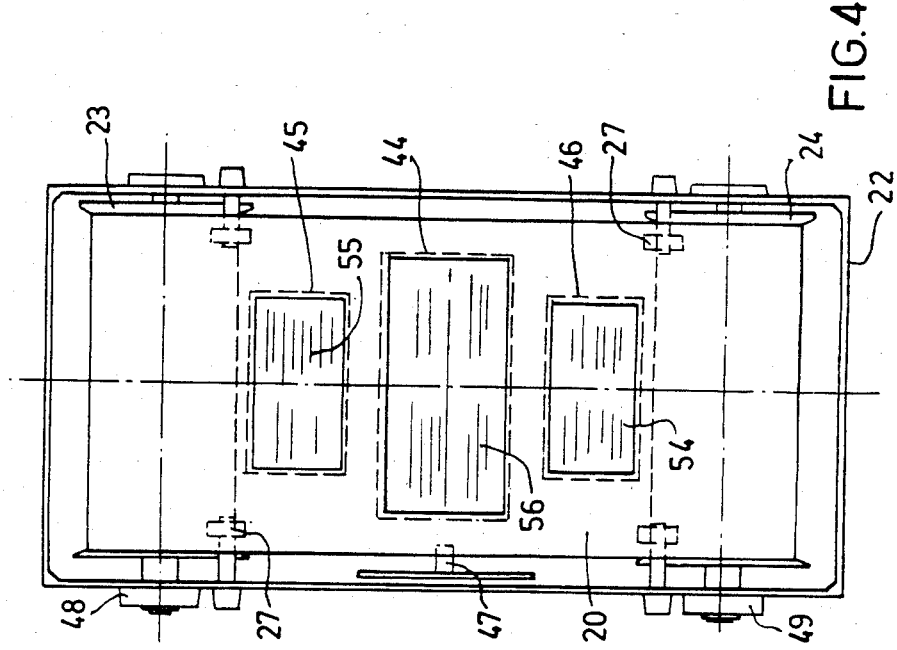
FIG. 4 is a planar view, on a larger scale, of the tape equipping the apparatus according to the invention the frontal face being raised.

Tape box 21 represented in further detail in FIGS. 4 to 6 also comprises film stretcher rollers 27 and fastening means and/or fixation means (not shown) allowing to removably fix it on a support of body 1 of the apparatus.

Figure 2:
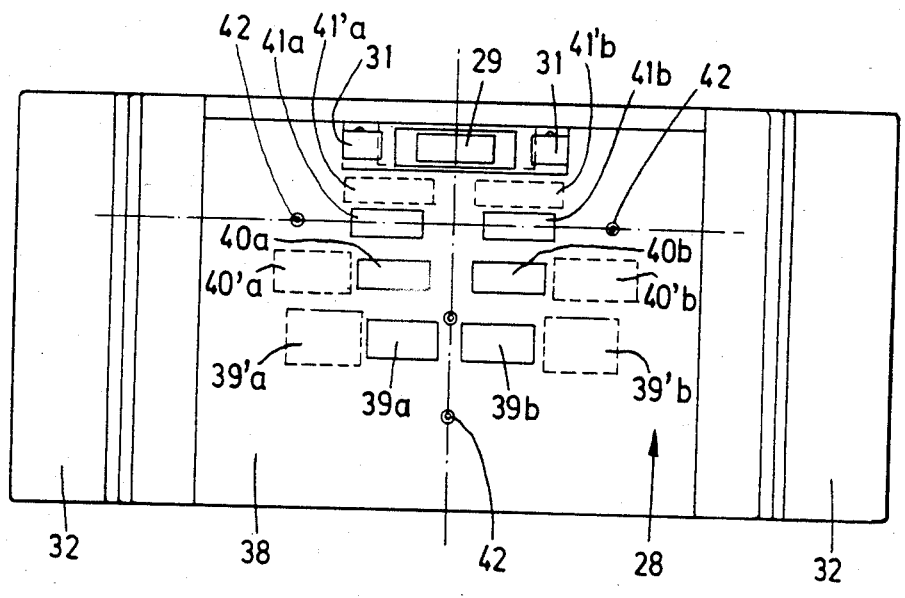
FIG. 2 is a view according to arrow B of FIG. 1, of the vision chamber of the apparatus shown in FIG. 1.
Figure 3:
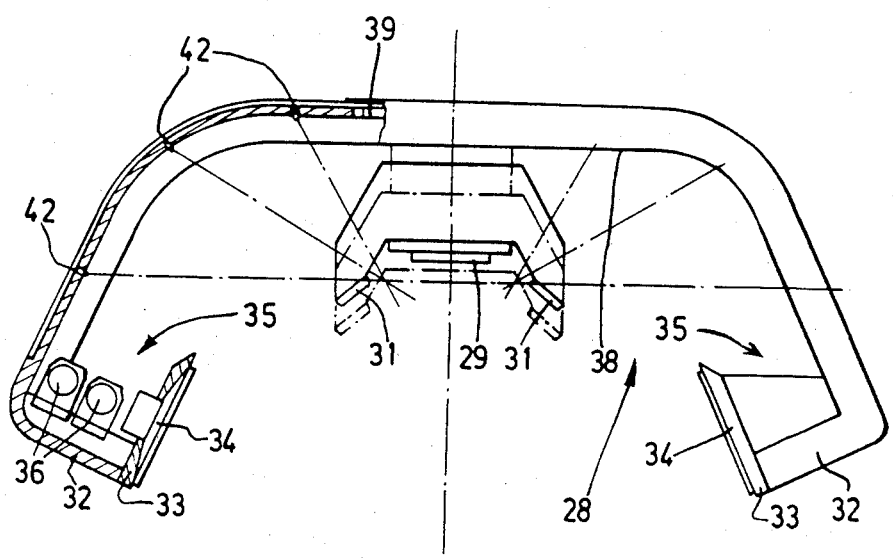
FIG. 3 is a planar view, partially in section, according to arrow A of FIG. 1, of the vision chamber of the apparatus.

On the left, according to FIG. 1, the body 1 of the sight testing apparatus according to the invention, presents a vision chamber 28 that, with reference to FIGS. 2 and 3, presents in a transversal cross-section the general form of a wide open U. At the centre of vision chamber 28 is disposed an adjustable head-rest constituted by a central part 29 forming a frontal rest for the patient's forehead, in principle non-adjustable by the patient but adjusted prior to testing by a braked screw 30 (cf. FIG. 1). The head-rest comprises two lateral rests 31 able to be applied on the sides of the forehead or the temples of the patient, and in principle adjusted by him.

Vision chamber 28 that is closed by lateral flanges 32 on the set off sides 33 of which it is possible to dispose loud-speakers 34 allowing to give a series of recorded instructions to the patient, forms kinds of lateral lighting cupboards 35 in which is disposed adjustable surroundings lighting constituted, for example, by fluoroescent tubes 36.

On its front face 38, vision chamber 28 presents three series of couples of openings 39 to 41, respectively (40a, 40b) for the input of intermediary distance vision path 6 (41a, 41b), for the input of the far vision path 13, and (39a, 39b) for the input of close vision path 2. Each of the openings of these couples 39 to 41 can be closed by a curtain or a shutter (39'a, 39'b, 40'a, 40'b, 41'a, 41'b)

such as shown by the broken lines of FIG. 2 and placed under the control of an operator or programmed by closing instructions. Face 38 of vision chamber 29 comprises, geometrically distributed in chosen sites around couples of openings 39 to 41, punctual or quasi-punctual light emitters 42, such as light emitting diodes LED allowing to detect potential field sight defects of each of the patient's eyes.

FIG. 4 shows the frontal plate of the removable tape box 21 which bears the bank of test-images and presents openings 44, 45 and 46 corresponding to openings 3, 7 and 14 of the body 1 of the apparatus and allows the vision of the test-images via the three vision paths 2, 6 and 13 (the openings are represented in dotted lines).

Openings 44 to 46 are larger than openings 3, 7 and 14 of the body, which they completely cover in service. By these openings 44 to 46, it is possible to control the state of the test-images once the tape box has been removed from the apparatus. An opening 47 provided in the frontal body of the tape box allows a cell (non show) of the apparatus, to control the position of the film 20 of the test-images, and especially to actuate it.

The series of questions presented to the patient can be carried on a magnetic recording tape unreeled in synchronization with film 20 that is put under tension by stretcher rollers 27 and can be unwound by motor means external to the tape box and coupled to the spools of said tape box by lateral coupling heads 48 and 49.

According to another embodiment shown in FIG. 5 and 6, one of the spools, for example spool 23 of tape box 21, is mechanically connected by irreversible driving means to an electric motor 50 that is either included in tape box 21 and fed by electric coupling (not shown), or integral with the apparatus and coupled to the spool at the time of positioning of spool 21. The other spool 24 mounted on bearings such as ball bearings, is coupled by its axis 51 to a strong spiral spring 52 fastened to an envelope 53 fixed to the body 22 of the tape box. Spool 24 is thus constantly biased toward the spooled position by spiral spring 52 and constantly stretches film 20. When electric motor 50 turns, it rotates spool 23, for example, in the winding on direction, while said spool pulls film 20, which causes spool 24 to turn against the force of spiral spring 52. Once electric motor 50 is no longer fed with current, output shaft 54 of its transmission is immobilized due to the blocking action of the irreversible transmission and spool 23 is immobilized. Spiral spring 52 maintains film 30 under tension and test-images 54, 55 and 56 respectively for far vision, intermediary distance vision and close vision are immobilized, perfectly plane and sharp. By feeding electric motor 50 with reversed voltage, its rotation direction is inversed, thus allowing spiral sping 52 to rotate spool 24 in the winding direction under the speed control of the irreversible transmission. On dismounting the tape box and uncoupling motor 50, film 20 is brought back to the wound position by spiral spring 52.

The operation of the apparatus will now be explained. A patient places his head in the correct position in vision chamber 28 by using adjustable lateral rests 31 and initiates, by using a start button (not shown) the cycle of the tape box 21.

Successive test-images thus pass before his eyes in close vision, far vision and intermediary distance vision, whereas loud-speakers 34 give him instructions and question him as to his vision for these test-images. By using convenient control buttons, the patient can interrupt the examination at given points, or even return to the previous phases of the examination. His replies to the questions are recorded on a magnetic recording tape, which, after the test is finished, can subsequently be listened to at leisure by an operator who will be able to check whether the responses to the questions asked correspond exactly to the tests presented and, in case of anomaly, advise the patient to consult an ophtalmologist for a more thorough examination.

The reactions of the patient to surroundings lighting by luminous cupboards 35 and punctual lighting-up of the diodes 42 can also be recorded on tape 21.

As a variant, a print-out machine can be connected to the apparatus, which machine allows to reconstitutein the form of a plain or punched card the patients responses.

Due to the provision of the spherical mirrors 12 and 18, it is possible to realize on the same images the examination of intermediary distance vision and far vision. In the case where the person who wishes to have his sight examined, for example a child, cannot use the apparatus himself, an operator controls the unwinding of the film 20 of tape box 21, asks the questions himself and records or notes the patient's responses. The reticence of patients to proceed regularly with a thorough examination of their sight is greatly reduced due to the apparatus according to the invention, since not only are the checking costs reduced, but above all the patient has the impression of proceeding himself, and at his own rhythm, with this test.

According to a more elaborate embodiment of the apparatus, tape box 21, with its two winding spools 23, 24, that is represented in vertical position with respect to the patient in FIG. 1, can be disposed horizontally according to an auxiliary fastening position that causes the images to be visioned by the patient to pass in front of opposite opening 3. In the example shown in FIGS. 1 and 2, the patient sees the images vertically or, sees them move in a vertical plane, whereas in the horizontal auxiliary disposition of tape box 21, the operator can cause the test-images to unwind horizontally in order to test the patients aptitude for visioning images in horizontal succession.

In order to allow various orientations of tape 21, it is advantageous to equip it with its own electric driving motor 50 rigidly fixed to the tape and connected by a flexible cable or brush and sliding contact connection to an adjustable electric network to allow to adjust, according to the wishes of the patient or the operator of the apparatus, the speed of unwinding and/or the stopping of film 20. It is thus possible to foresee a tape box 21 fixed on body 1 of the apparatus but orientable in any direction in a displacement and successive moving plane of the film 20.

Of course, the present invention is in no way limited to the realisations described and represented; it is adaptable to numerous variants available to a man skilled in art, according to the applications envisaged and without departing from the spirit and scope of the invention.

We claim:

1. Apparatus for detecting visual deficiencies of the eyes of a patient, comprising:
a cabinet having a cassette receiving surface with (i) a close vision path test image receiving portion, (ii) an intermediate vision path test image receiving portion, and (iii) a far vision path test image receiving portion, said cabinet also having a vision chamber receiving surface remote from said cassette receiving surface;

a removable cassette disposed adjacent the cassette receiving surface of said cabinet, said cassette containing a tape or film having thereon a series of close vision test images and a series of intermediate/far vision test images, said tape or film being wound on two rotatable winding spools spaced apart from each other and positioned so that (i) a portion of the tape film extending between the spools is disposed along said test image receiving portions of said cassette receiving surface of said cabinet, (ii) one of said close vision test images is adapted to be positioned at said close vision path test image receiving portion of said cassette receiving surface, and (iii) one of said intermediate/far vision test images is adapted to be positioned at said intermediate vision path test image receiving portion and at said far vision path test image receiving portion of said cassette image receiving surface of said cabinet;

illumination means for illuminating said test images;

a vision chamber housing attached to said cabinet, said housing defining a vision chamber therein and having a viewing surface adjacent the vision chamber receiving surface of the cabinet, said vision chamber housing being adapted to receive at least a portion of the head of a patient with the eyes of the patient disposed at predetermined locations within the housing;

an optical system disposed within said cabinet and comprising:

a close vision optical path having a given optical length for optically coupling a close vision test image at said close vision path test image receiving portion of said cassette receiving surface to at least one of said predetermined locations within said vision chamber housing, an intermediate vision optical path having an optical length greater than that of said close vision optical path for optically coupling an intermediate/far vision test image at said intermediate vision path test image receiving portion of said cassette receiving surface to at least one of said predetermined locations within said vision chamber housing, said intermediate vision optical path comprising at least one concave spherical mirror for increasing the optical length of said intermediate vision optical path, and a far vision optical path having an optical length greater than that of said intermediate vision optical path for optically coupling an intermediate/far vision test image at said far vision path test image receiving portion of said cassette receiving surface to at least one of said predetermined locations within said vision chamber housing, said far vision optical path comprising at least one concave spherical mirror for increasing the optical length of said far vision optical path; and spool drive means for rotating at least one of said spools to position a desired one of said test images at a corresponding test image receiving portion of said cassette receiving surface of said cabinet, whereby the same test image is employed for testing the intermediate vision and the far vision of the patient.

2. The apparatus according to claim 1, further comprising a vision surface in said vision chamber having final openings, said vision surface being disposed adjacent said predetermined locations so that said final openings are in front of the patient's eyes when the patient's head is within the vision chamber housing, and means for selectively closing said final openings.

3. The apparatus according to claim 1, wherein said vision chamber housing includes an adjustable rest for the forehead of the patient to maintain the center of rotation of each of the patient's eyes at the predetermined location for the corresponding eye.

4. The apparatus according to claim 1, further comprising:

lighting means withing the vision chamber housing for producing a luminous ambiance therein; and audio apparatus synchronized with said spool drive means and adapted to be disposed adjacent at least one ear of the patient, for giving the patient instructions and asking the patient questions as various test images are disposed at said test image receiving portions of said cassette receiving surface of said cabinet.

5. The apparatus according to claim 4, further comprising means for recording the patient's responses to the questions asked by said audio apparatus on a record medium band operatively associated with said cassette and movable in sychronism with the tape or film therein.

6. The apparatus according to claim 2, further comprising substantially point sources of light disposed in said vision chamber between said final openings and visible to the patient, for permitting the detection of potential field sight defects of each of the patient's eyes.

7. The apparatus according to claim 1, further comprising means enabling orientation of said cassette in a plurality of angular positions adjacent said cassette receiving surface of said cabinet, said spool drive means comprising a motor connected to said cassette and mechanically adjustable means for connecting said motor to a power source while permitting relative movement therebetween, so as to allow the tape or film to pass at least one of said test image receiving portions of said cassette receiving surface along corresponding directions with respect to the patient's eyes.

8. The apparatus according to claim 1, further comprising at least one tensioning roller engaging the portion of said tape of film extending between said spools, the tape or film within the cassette being at least partially transparent, said illumination means being disposed within said cassette for illuminating the test images by transmission of light through the tape or film toward said cassette receiving surface of said cabinet, means for coupling said illumination means to a power source therefor.

9. The apparatus according to claim 8, further comprising cassette spool biasing means for urging one of said spools in a tape or film winding direction thereof, and an unreeling motor connected to the other of said spools via unidirectional transmission means, so that the tape or film is maintained in constant tension while being movable to any desired position by rotation of said spools.

10. An apparatus for examining and detecting visual deficiencies of a patient's eyes, comprising:

a body;

three different fixed vision paths in said body for checking sight at a close distance, a far distance and an intermediate distance, respectively;

test image openings in said body associated with each vision path;

means for positioning test images in front of said test image openings;

light means for projecting said test images through said test image openings to the different vision paths;

each vision path including at least one mirror for reflecting the respective projected test images to said patient's eyes;

at least one vision path including a concave mirror which makes the projected test image appear to emanate from a farther distance; and a vision chamber for supporting the patient's head at a preset position at which the patient can view the reflected test images from any of said three paths.

* * * * *